United States Patent
Eilos et al.

(10) Patent No.: US 7,473,811 B2
(45) Date of Patent: Jan. 6, 2009

(54) PROCESS FOR THE HYDROGENATION OF OLEFINS

(75) Inventors: Isto Eilos, Porvoo (FI); Antti Pyhälahti, Helsinki (FI); Matti Nurminen, Porvoo (FI); Veli-Matti Purola, Hamari (FI)

(73) Assignee: Neste Oil Oyj, Espoo (FI)

( * ) Notice: Subject to any disclaimer, the term of this patent is extended or adjusted under 35 U.S.C. 154(b) by 644 days.

(21) Appl. No.: 10/986,368

(22) Filed: Nov. 12, 2004

(65) Prior Publication Data

US 2005/0177014 A1    Aug. 11, 2005

Related U.S. Application Data

(60) Provisional application No. 60/519,281, filed on Nov. 13, 2003.

(51) Int. Cl.
    C07C 5/03  (2006.01)
(52) U.S. Cl. ..................................................... 585/265
(58) Field of Classification Search .................. 585/265
    See application file for complete search history.

(56) References Cited

U.S. PATENT DOCUMENTS

| | | | |
|---|---|---|---|
| 3,696,022 A | 10/1972 | Hutchings | |
| 4,014,783 A | 3/1977 | Rausch | |
| 4,211,634 A | 7/1980 | Bertolacini et al. | |
| 4,960,960 A * | 10/1990 | Harrison et al. | 568/881 |
| 5,019,357 A | 5/1991 | Harandi et al. | |
| 5,093,535 A | 3/1992 | Harrison et al. | |
| 5,789,643 A | 8/1998 | Herwig et al. | |
| 6,190,542 B1 | 2/2001 | Comolli et al. | |
| 6,329,561 B1 | 12/2001 | Webber et al. | |
| 6,548,721 B1 | 4/2003 | Mc Culloch et al. | |
| 6,613,108 B1 | 9/2003 | Aittamaa et al. | |

FOREIGN PATENT DOCUMENTS

| | | |
|---|---|---|
| CN | 94102955.7 | 10/1995 |
| EP | 0323032 A2 | 7/1989 |
| EP | 1184361 A1 | 3/2002 |
| FI | 106955 B | 5/2001 |
| GB | 1044771 | 10/1966 |
| WO | WO 02/26669 A1 | 4/2002 |
| WO | WO 2004/033399 A1 | 4/2004 |

OTHER PUBLICATIONS

"1-4-Butylene-glycol Technology of Linde/Yukong", "Ethylene Industry", 1995, 7(3), 58-63.

* cited by examiner

*Primary Examiner*—Thuan Dinh Dang
(74) *Attorney, Agent, or Firm*—Birch, Stewart, Kolasch & Birch, LLP

(57) ABSTRACT

The present invention relates to a process for the hydrogenation of olefins. The process comprises hydrogenation of a feed stock comprising more than 90 wt-% of olefins, carried out in a hydrogenation reactor comprising at least two reaction stages, wherein the feed stock is hydrogenated in the first reaction stage equipped with a cooling circuit and comprising a first and an optional second catalyst bed, and the effluent from the first reaction stage is hydrogenated in the final reaction stage comprising one or more catalyst beds and optionally equipped with a cooling circuit, the process is operated in trickling or pulse flow mode in a three phase reactor with a fixed catalyst bed and at least one catalyst of same or different type is used in each stage, the catalyst having different particle size and/or optionally different shape in at least two stages.

19 Claims, 4 Drawing Sheets

PROCESS FOR THE HYDROGENATION OF OLEFINS

This Non-provisional application claims priority under 35 U.S.C. § 119(e) on U.S. Provisional Application No. 60/519,281 filed on Nov. 13, 2003, the entire contents of which are hereby incorporated by reference.

FIELD OF THE INVENTION

The present invention relates to a process for the hydrogenation of olefins and particularly to a process for the hydrogenation of isooctene.

STATE OF THE ART

Several methods are known in the prior art for the production of isooctane and for the dimerization of isobutene. A process for the manufacture of isooctane from a hydrocarbon feed stock containing isobutene is disclosed in FI 106955. Accordingly the hydrocarbon feed stock is brought into contact with an acidic catalyst, preferably a cationic ion-exchange resin, in the presence of an oxygenated compound at conditions wherein at least part of the isobutene is dimerized into diisobutene, which is then separated and hydrogenated to isooctane.

U.S. Pat. No. 6,329,561 teaches a method of producing high purity isooctane, useful as gasoline blending component, from diisobutene or isooctane contaminated with minor amounts of oxygenated impurities. This method comprises converting the oxygenated impurities at conditions of elevated temperature and pressure in either a one-step or a two-step process, over a hydrogenation catalyst, to hydrocarbon and water and recovering the purified diisobutene or isooctane stream.

Typically the product obtained from a butene dimerization unit contains as impurities 0.1-5 wt-% of oxygenated impurities such as ethers, alcohols, ketones and the like and minor amounts of sulphur containing compounds. These impurities effect on the utility of the product, isooctane, as gasoline blending component.

GB 1044771 discloses a method of removing sulphur compounds from a hydrocarbon feed stock by hydrogenating sulphur containing compounds present in the feed stock with hydrogenating gas over a hydrodesulphurization catalyst, such as a molybdenum catalyst supported on alumina, which hydrocarbon feed stock and/or hydrogenating gas contains olefins and/or carbon oxides. This method comprises passing a mixture of hydrocarbons in vapour form with the hydrogenating gas over the hydrodesulphurization catalyst to convert the sulphur present into hydrogen sulphide and removing the hydrogen sulphide.

WO 2004/033399 discloses a process for simultaneous hydrogenation of olefins and degradation of oxygenated impurities and sulphur compounds by hydrogenolysis. A feed stock containing 80-97 wt-% of C8 olefins, 3-20 wt-% of C12 olefins, 0.1-7 wt-% of C9, C10, C11 and heavier>C12 olefins, and optionally minor amounts of lighter C6-C7 olefins was used.

Suitable hydrogenation catalysts were noble metal and nickel catalysts on aluminium oxide support and preferable metals were platinum and palladium, particularly preferably platinum.

In the process the feed stock was hydrogenated in two steps. In the first step the major part of C8 olefins was converted but the conversion of heavier olefins, oxygenated impurities and sulphur compounds was rather low. In the second step the remaining C8 olefins, C12 olefins and other heavier olefins, oxygenated impurities and sulphur compounds reacted.

In the first step the product stream was optionally circulated in order to dilute the concentrated olefin feed, and thereby reaction heat was removed safely from the saturation of double bonds.

The reaction temperature in the first step was 150-230° C. and the pressure range was 20-70 bar. In the second step a higher reaction temperature was applied in the reactor than in the first step. The temperature was 190-260° C. and the pressure range was 20-70 bar. In the beginning of this process the reaction is vigorous and at the end the reaction is very slow. When one very active catalyst, such as an expensive noble metal catalyst having a certain particle size is used in the process, rapid formation of coke takes place particularly in the beginning of the process, which results in the deactivation of the catalyst.

From the state of the art it can be seen that internal gas/liquid flows vary to a great extent in reactor sections. It is difficult to gain good reactor performance in every reactor section because of different hydraulic requirements.

None of the prior art publications teach a simple and effective process for simultaneous hydrogenation of olefins and removal of oxygenated impurities and sulphur containing compounds and thus it can be seen that there exists an evident need for such a process.

OBJECT OF THE INVENTION

An object of the invention is a process for the hydrogenation of olefins.

A further object of the invention is to provide reactor arrangement for the hydrogenation of olefins.

A still further object of the invention is to provide an improved process for the hydrogenation of olefins, wherein the disadvantages and problems relating to the processes according to the state of the art can be avoided or at east significantly reduced.

A still further object of the invention is to provide a process for the hydrogenation of isooctene.

Characteristic features of the process and reactor arrangement according to the invention are provided in the claims.

SUMMARY OF THE INVENTION

The process according to the invention for the hydrogenation of olefins comprises hydrogenation, which is carried out in a hydrogenation reactor comprising at least two stages, wherein a feed stock comprising at least 90 wt-% of olefins is hydrogenated in a three phase reactor with a fixed catalyst bed, operating in trickling or pulse flow mode and at least one catalyst of same or different type is used in each stage, the catalyst having different particle size in at least two stages and/or optionally different shape in at least two stages.

The feed stock comprises typically from 0 to 80 wt-% and preferably from 0 to 20 wt-% of C4 to C7 olefins, from 0 to 99 wt-%, preferably from 80 to 99 wt-% of C8 olefins, and from 0 to 30 wt-%, preferably from 0 to 10 wt-% of heavier than C8 olefins.

DETAILED DESCRIPTION OF THE INVENTION

Figure 1:
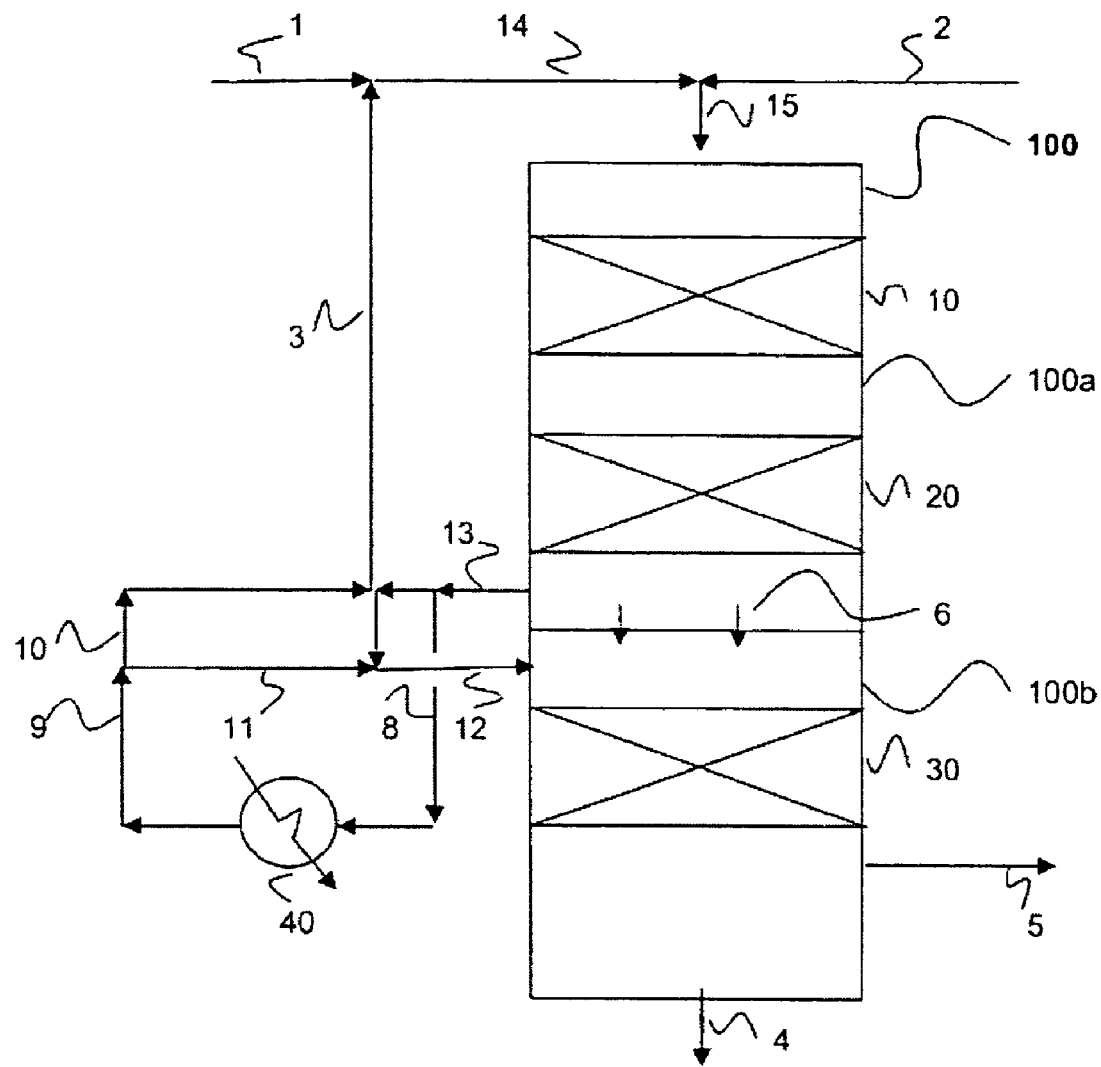
FIGS. 1-4 illustrate alternative embodiments of reactor arrangements for a hydrogenation process according to the invention.

It has been surprisingly found that the deficiencies and problems relating to the processes according to the state of the art can be avoided or at least significantly decreased using the process according to the invention. The process according to the invention comprises hydrogenation of a feed stock comprising more than 90 wt-% of olefins, carried out in a hydrogenation reactor comprising at least two reaction stages, wherein the feed stock is hydrogenated in a the first reaction stage equipped with a cooling circuit and comprising a first and an optional second catalyst bed, and the effluent from the first reaction stage is hydrogenated in the final reaction stage comprising one or more catalyst beds and optionally equipped with a cooling circuit, hydrogen is fed to the first reaction stage or to the final reaction stage or to both reaction stages, the process is operated in trickling or pulse flow mode in a three phase reactor with a fixed catalyst bed and at least one catalyst of same or different type is used in each stage, the catalyst having different particle size and/or optionally different shape in at least two stages.

The particle size means here particle size distribution, which is measured for example by sieve methods, laser diffraction methods or other methods known in the art. A catalyst having a desired particle size and optionally desired shape may be manufactured and used.

The shape of the catalyst particles may vary and extrudates, tablets, spherical and oval particles are typically used.

The reactor arrangement for the hydrogenation of olefins according to the invention comprises a hydrogenation reactor operating in trickling or pulse flow mode in a three phase reactor with a fixed catalyst bed and comprising at least two reaction stages, wherein the first reaction stage is equipped with a cooling circuit and comprising a first and an optional second catalyst bed, and the final reaction stage comprises one or more catalyst beds and it is optionally equipped with a cooling circuit, and at least one catalyst of same or different type is used in each stage, the catalyst having different particle size and/or optionally different shape in at least two stages.

The feed stock comprises typically from 0 to 80 wt-% and preferably from 0 to 20 wt-% of C4 to C7 olefins, from 0 to 99 wt-%, preferably from 80 to 99 wt-% of C8 olefins, and from 0 to 30 wt-%, preferably from 0 to 10 wt-% of heavier than C8 olefins. The feed stock is a mixture of olefins which may be obtained from a butane dimerization unit, however the origin of the feed stock is not limited.

Preferably the feed stock comprises more than 50 wt-% of di-isobutylene and tri-isobutylene and not more than 30 wt-% of other olefins. Optionally the feed stock comprises iso-butylene and n-butylene, as well as codimers of iso-butylene and n-butylene.

The process comprises hydrogenation, which is carried out in a hydrogenation reactor comprising at least two stages. In the first process stage the hydrogenation of the feed stock, such as iso-butylene dimers, is carried out. The first reaction stage comprises a first and an optional second catalyst bed, and it is equipped with a cooling circuit. In the first stage typically more than 50 wt-% and preferably more than 80 wt-% of the iso-butylene dimers are hydrogenated.

In the final reaction stage the hydrogenation of the slowly reacting components of the feed stock, such as iso-butylene trimers is carried out. The final reaction stage comprises one or more catalyst beds and optionally it is equipped with a cooling circuit or in the final stage there may be no cooling circuit or it is at least 30% smaller than that in the first stage.

The hydrogenation reactor consists of two or more reaction stages. Optionally the reaction stages can be divided into two reactor or more vessels. The reaction takes place in trickling or pulse flow state where the gas is the continuous or semi-continuous phase and the liquid flows along the catalyst surfaces.

Each reaction stage comprises at least one catalyst bed and the catalyst bed consists of one or multiple catalyst layers and preferably the amount of catalyst beds in each reaction stage is from one to three. The catalyst beds may be in the same reactor vessel or the catalyst beds may be in different reactor vessels.

The hydrogenation reaction is an exothermic reaction and therefore each reaction stage may optionally be cooled. In the first reaction stage, where most of the hydrogenation reactions take place, the cooling is carried out preferably with cooled recycle, which arrangement gives the best possibility to avoid forming of coke on the catalyst. If intermediate reactor cooling between the catalyst beds is used, the recycling flow can be decreased or eliminated. Preferably the cooling of the hydrogenation reactor is accomplished with a cooling system located between the multiple catalyst beds. In the final reaction stage the released heat of the reaction is typically low and therefore normally no cooling is required. The feed stock may optionally be diluted using process streams.

The ratio of liquid and gas flows and flow rates differs considerably in the reaction stages. The height/diameter ratio of the catalyst bed affects the liquid/gas distribution in it. If a catalyst having the same particle size were used in the catalyst beds, optimal hydraulic requirements of the diameter/height ratios in the reaction stages would vary substantially and the flow regimes in different reactor sections might not be optimal. This would lead to the requirement for reactor parts having a different diameter. For this reason it is necessary to use a catalyst or catalysts with different particle size in different catalyst beds. This results in that the catalyst bed heights can be made smaller and consequently the liquid/gas distribution through the catalyst bed will be more equal. Further, the equal distribution gives a possibility to minimize the consumption of hydrogen.

According to the invention the particle size of the catalyst in each catalyst bed in each reaction stage is chosen on hydrodynamic grounds so that the catalyst bed height/diameter ratio will be between 1 and 20 and the fluid flow regime for designed feed rate is trickling or pulsing flow and the bed pressure drop is optimal. In the first reaction stage preferably the catalyst particle size is larger than the catalyst particle size in the final reaction stage. In the final stage the reaction kinetics favours smaller catalyst particle size and a high activity catalyst. The difference in the diameter of the reactor of the first stage and of the final stage is minimized using a catalyst or catalysts with different particle size. Typically the catalyst particle size ranges between 1 and 10 mm.

Figures

The invention is illustrated with the following examples presenting preferable embodiments depicted in attached FIGS. 1, 2, 3 and 4, with preferable reactor arrangements. Combinations and variations of these examples form also possible embodiments of the invention as well as embodiments where the catalysts in different reaction stages are located in separate vessels.

In FIG. 1 a basic case is described wherein olefin stream 1, hydrogen stream 2 and recycle stream 3 are mixed together and fed into the first reaction stage 100*a* of the hydrogenation reactor 100. The mixing order of the streams 1, 2 and 3 may differ from the one shown in the FIG. 1, or all streams 1, 2 an 3 may be fed directly to the reaction stage 100a and mixed inside it. The first reaction stage 100a consists of catalyst beds 10 and 20. The liquid phase of the first reaction stage 100a, effluent 13, is partly fed to the cooler 40 via line 8 and partly by-passed the cooler 40. Part of the effluent 13 is circulated as recycle strewn 3 to the first reaction stage 100a feed for controlling temperature rise in the catalyst beds 10 and 20 and the rest is fed as stream 12 to the second (final) reaction stage 100b. The gas effluent 6 of the first reaction stage 100a, containing traces of liquid phase, is directly fed to the second reaction stage 100b through holes or pipe(s) between the reaction stages 100a and 100b.

The portion of liquid effluent 13, stream 12, and effluent gas 6 from the reaction stage 100a are fed to the reaction stage 100b containing catalyst bed 30. The gaseous reactor effluent 5 and liquid effluent 4 are separated from each other at the bottom of the reaction stage 100b. Both streams 4 and 5 are in a conventional manner fed to by-product purification and hydrogen separation procedures known in the art.

Figure 2:
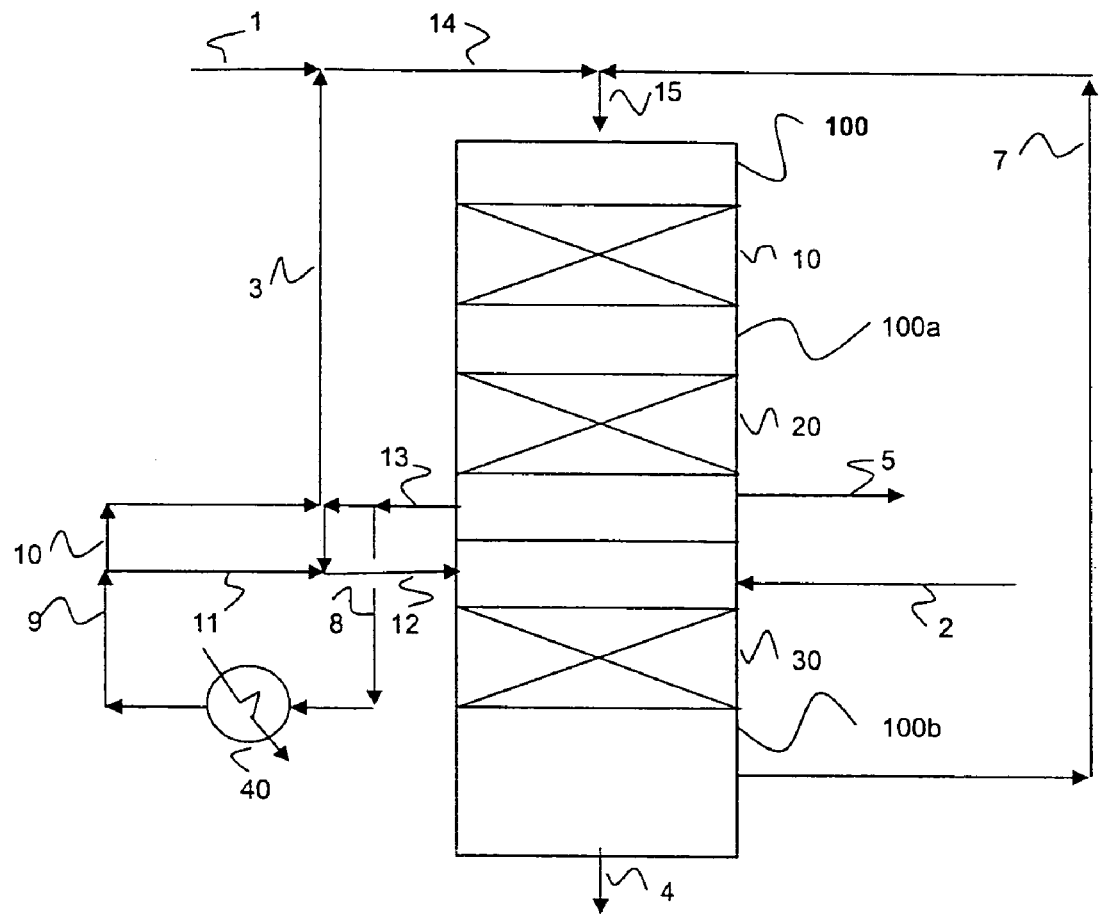

In FIG. 2 a particularly preferable arrangement is described wherein maximal olefin conversion is achieved by feeding fresh hydrogen 2 into the final reaction stage 100b. Olefin stream 1, gas flow containing unconsumed hydrogen from the final reaction stage 100b as stream 7 and recycle stream 3 are mixed together and fed into the first reaction stage 100a of the hydrogenation reactor 100. The mixing order of the streams 1, 7 and 3 may differ from the one shown in the FIG. 2 or all streams 1, 7 and 3 may be fed directly to the reaction stage 100a and mixed inside it. The first reaction stage 100a consists of catalyst beds 10 and 20. The liquid phase of the first reaction stage 100a, effluent 13, is partly fed to the cooler 40 via line 8 and partly by-passed the cooler 40. Part of the effluent 13 is circulated as recycle stream 3 to the first reaction stage 100a feed for controlling temperature rise in the catalyst beds 10 and 20 and the rest is fed as stream 12 to the second reaction stage 100b. The hydrogenated product is taken in liquid phase, stream 4, from the bottom of final reaction stage 100b and the gas flow, containing unconsumed hydrogen from the final reaction stage 100b, is conducted as stream 7 to the first reaction stage 100a feed. The liquid product of the first reaction stage 100a, stream 13 and gaseous product 5 are separated from each other at the bottom part of the first reaction stage 100a. Both streams 4 and 5 are in a conventional manner fed to optional by-product purification and hydrogen separation procedures known in the art.

Optionally part of fresh hydrogen (stream 2) is fed into the first reaction stage 100a (not shown in the figure). The operating pressure in the final reaction stage 100b is higher than that in the first reaction stage 100a. The required pressure difference can be maintained by liquid head or by using a recycle pump.

Figure 3:
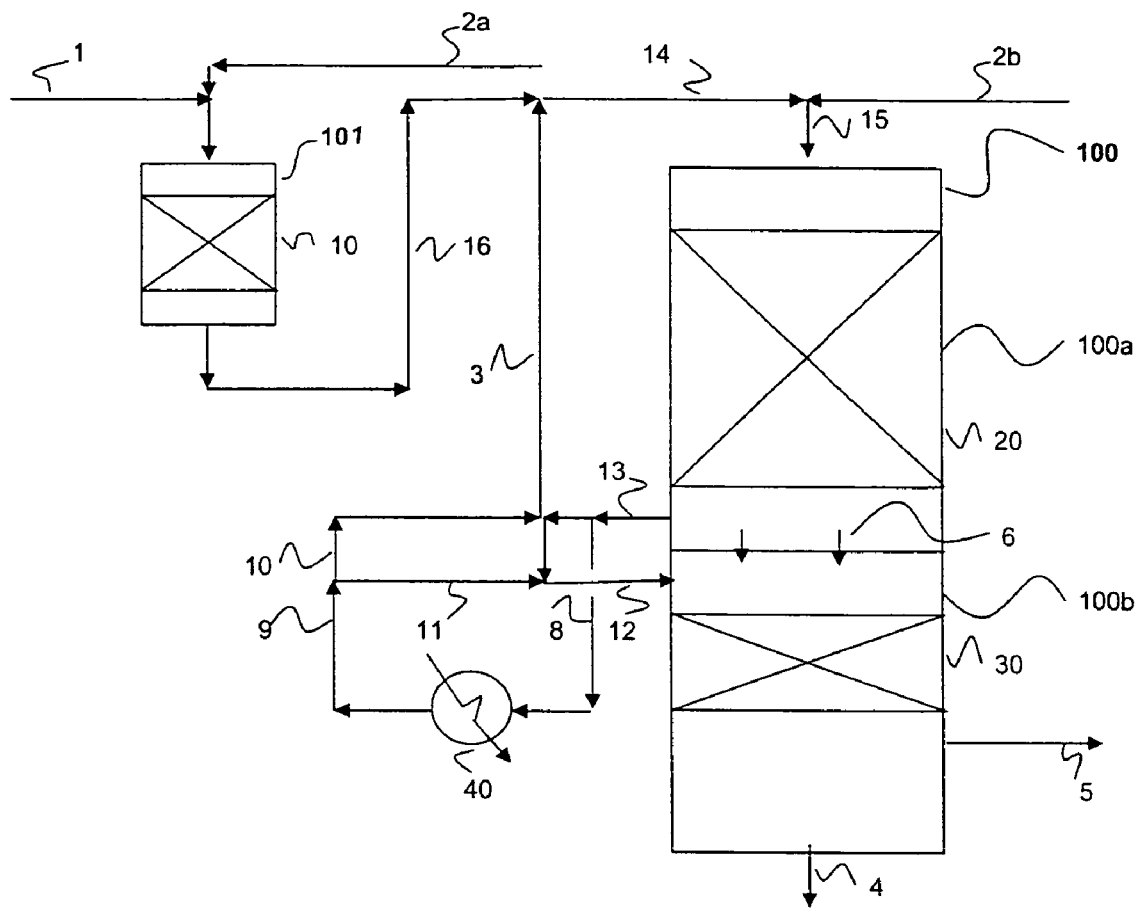

In FIG. 3 an alternative process from the one described in FIG. 1, is presented wherein the catalyst bed 10 from the first reaction stage 100a, is installed in a separate vessel 101 before the reactor vessel 100. Olefin stream 1 and hydrogen stream 2a are mixed together and fed to the catalyst bed 10 in vessel 101. The effluent from vessel 101 as stream 16, recycle stream 3 and hydrogen stream 2b are mixed together and fed into the first reaction stage 100a of the hydrogenation reactor 100. The mixing order of the streams 16 and 3 may differ from the one shown in the FIG. 3 or streams 16 and 3 may fed directly to the reaction stage 100a and mixed inside it. The first reaction stage 100a consists of catalyst bed 20. The liquid phase of the first reaction stage 100a, effluent 13, is partly fed to the cooler 40 via line 8 and partly by-passed the cooler 40. Part of the effluent 13 is circulated as recycle stream 3 to the first reaction stage 100a feed for controlling temperature rise in the catalyst bed 20 and the rest is fed as stream 12 to the second reaction stage 100b. The gas effluent 6 of the first reaction stage 100a containing traces of liquid phase is directly fed to the second reaction stage 100b through holes or pipe(s) between the reaction stages 100a and 100b.

The portion of liquid effluent 13, stream 12, and effluent gas 6 from the reaction stage 100a are fed to the reaction stage 100b containing catalyst bed 30. The gaseous reactor effluent 5 and liquid effluent 4 are separated from each other at the bottom of the reaction stage 100b. Both streams 4 and 5 are in a conventional manner fed to optional by-product purification and hydrogen separation procedures known in the art.

The use of the separate hydrogenation reactor 101 results in that the size of the reactor 101 and catalyst bed 10 are smaller as the recycle stream 3 is not circulating through it. Fresh hydrogen stream 2a is preferably mixed with feed stream 1 before the catalyst bed 10 or hydrogen stream may be stream 2b mixed with reactor 100 feed, stream 14 (not shown in the figure). One alternative is to feed part of fresh hydrogen via line 2a and rest via line 2b.

Figure 4:
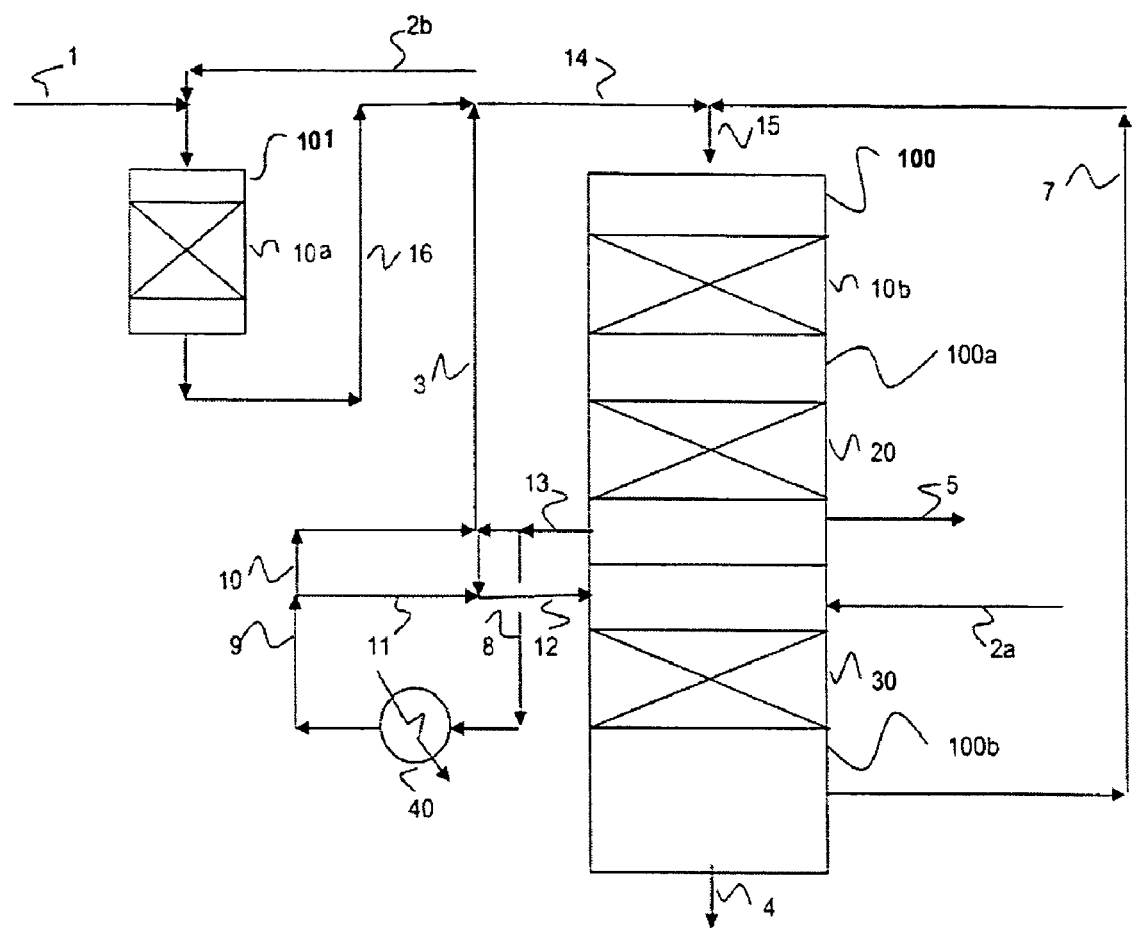

In FIG. 4 an alternative process from the one described in FIG. 2, is presented. Catalyst bed 10a of the first reaction stage is installed in a separate vessel, reactor 101, before the reactor vessel 100. Olefin stream 1 and hydrogen stream 2b are mixed together and fed to the catalyst bed 10a in the reactor 101. The effluent from reactor 101, as stream 16, gas flow containing unconsumed hydrogen from the final reaction stage 100b, as stream 7, and recycle stream 3 are mixed together and fed into the first reaction stage 100a of the hydrogenation reactor 100. The mixing order of the streams 16, 7 and 3 may differ from the one shown in FIG. 4 or all streams 16, 7 an 3 may be fed directly to reaction stage 100a and mixed inside it. The first reaction stage 100a consists of catalyst beds 10b and 20. The liquid phase of the first reaction stage 10a, effluent 13, is partly fed to the cooler 40 via line 8 and partly by-passed the cooler 40. Part of the effluent 13 is circulated as recycle stream 3 to the first reaction stage 100a feed for controlling temperature rise in the catalyst beds 10b and 20 and the rest is fed as stream 12 to the second reaction stage 100b. The hydrogenated product is taken in liquid phase, stream 4, from the bottom of final reaction stage 100b and the gas flow, containing unconsumed hydrogen from the final reaction stage 100b is conducted as stream 7 to the first reaction stage 100a feed. The liquid product of the first reaction stage 100a, stream 13, and gaseous product 5 are separated from each other at the bottom part of first reaction stage 100a. Both streams 4 and 5 are in a conventional manner fed to optional by-product purification and hydrogen separation procedures known in the art.

Optionally part of fresh hydrogen (stream 2a) is fed into the first reaction stage 100a (not shown in the figure). The operating pressure in the final reaction stage 100b is higher than that in the first reaction stage 100a. The required pressure difference can be maintained by liquid head or by using a recycle pump.

This results in that the size of reactor 101 and catalyst bed 10a is smaller as the recycle stream 3 is not circulating through it. Preferably part of fresh hydrogen stream is mixed with feed stream 1 before catalyst bed 10a via line 2b. One alternative is to feed all of fresh hydrogen to reaction stage 100b as stream 2a (not shown in the figure).

Catalyst Beds

The height and diameter of the catalyst beds are chosen on reaction kinetics and optimal liquid/gas flow or pattern and pressure drop. The catalyst beds may consist of one or more layers of different solid absorption materials, or/and one or different hydrogenation catalysts. The catalyst layers in the beds may differ from each other by particle size or shape or activity or active sites of material. Inert particles may be used above and below each bed to improve fluid distribution.

If the catalyst beds are located in different reactor vessels, the diameter of the reactor can vary between the catalyst beds in the reaction stages. Preferably at least one catalyst bed of the first reaction stage is installed in a separate vessel before the hydrogenation reactor. Preferably the diameter of the reactor vessel before the final reactor (containing catalyst bed 20 in FIGS. 1 and 2) is the same or not more than 50% and particularly preferably not more than 20% larger than the one of the final reactor vessel (containing catalyst bed 30 in FIGS. 1 and 2). Preferably all reaction stages are located in the same housing.

Catalyst Bed 10

This bed is optional and its main operational function is to trap the impurities contained in the feed, harmful to the hydrogenation catalyst, e.g. inorganic acidic sulphur compounds that possibly originate from the catalyst of the isobutylene dimerization process preceding the hydrogenation stage. The first catalyst bed 10 is protected by alkaline adsorption or absorption material which means that the catalyst particles of the layer(s) in this bed are typically either alkaline, for example alumina particles, or this catalyst bed may comprise a hydrogenation catalyst having lower activity, or less active catalyst as used in bed 20 or absorbent, such as active carbon particles may be used. The particle size and shape for the catalyst in the layers of this bed may be chosen freely.

Each catalyst bed, particularly catalyst bed 10 may have different layers of different catalysts or catalyst/adsorbent/inert material combinations.

Catalyst Bed 20

The particle size of the hydrogenation catalyst in this bed is chosen on hydrodynamic basis to be as large as is practical and the catalyst particle size for this bed is typically 1 . . . 10 mm, preferably 2 . . . 5 mm.

In the reaction stage utilizing catalyst bed 20 typically the main part of iso-octene is hydrogenated. Suitable catalysts are nickel-based catalysts, particularly at the lower reaction temperature range and noble metal (platinum, palladium or combination of those) based catalysts at the higher reaction temperature range. The process temperature depends on catalyst type used and the degree of activity of the catalyst. It is typically 100-150° C. if nickel catalyst is used, and 130-200° C. for noble metal catalyst (Pt, Pd or Pd/Pt-catalyst). The deactivation of the catalyst during the run may be compensated by raising the process temperature.

In the alternative embodiments of the process, wherein there is no catalyst bed 10 in the hydrogenation reactor 100, guard bed material for trapping particles and impurities of feed and/or hydrogen stream may be used on the surface of the catalyst layer of catalyst bed 20. Guard bed materials are commercially available, such as Norton Macro Trap™ typically comprising highly macroporous material or similar. The particle size of the guard bed material is larger than particle size of the catalyst and the height of the layer of the guard bed material is typically from 0.1 m to 1 m.

Catalyst Bed 30

In the final catalyst bed the hydrogenation of slowly reacting components of the feed stock, like residual iso-octene, iso-butylene trimers, iso-butylene tetramers, oxygenates and sulphur components takes place. This reaction stage requires the most active hydrogenation catalyst and high hydrogen partial pressure and/or the hydrogenation can be performed at a higher temperature than in previous catalyst beds. Because of the low olefin content and low heat production compared to catalyst bed 20, this bed requires no cooling circulation. Because of the lower liquid load the catalyst can be chosen to have a smaller particle size than in the previous catalyst beds, being typically 1-3 mm. In this stage the process temperature is 150° C.-250° C. In terms of temperature the same circumstances apply to this stage as to bed 20. It is preferable to use low hydrogen and olefin concentration in the final stage.

The catalyst particle size used in this bed is smaller than or equal to the particle size used in bed 20. Equal particle size in catalyst beds 20 and 30 would require smaller cross sectional area in bed 30 than in bed 20.

It is preferable in some cases that all catalyst layers and beds have different catalysts and catalyst activities, but same catalyst may also be used.

The pressure ranges typically between 20 and 70 bar in the process.

Operation Mode of the Reactor

The hydrogenation reactor is designed to function in trickling or pulsing state where the gaseous phase is continuous or semi-continuous and the liquid phase flows along the solids surfaces, mainly catalyst surfaces, wetting them efficiently.

This operation mode ensures that gaseous hydrogen has access to the whole volume of the reactor and an excellent mass transfer rate both between liquid and gaseous phase and liquid and solids phase is achieved. In the operation mode where liquid is continuous phase, it is necessary to maintain high hydrogen excess in order to guarantee that hydrogen is not completely depleted in any part of the reactor. Preferably the reactor is operated with not more than 40 mole % hydrogen excess and no circulating gas compressor is needed, particularly preferably the hydrogen excess is less than 20%.

Either more than 50 v/v % of the fresh hydrogen is introduced to the first reaction stage of the hydrogenation reactor or more than 50 v/v % of the hydrogen is introduced to the final reaction stage of the hydrogenation reactor.

When the gas phase is continuous or semi-continuous, this hydrogen excess can be significantly reduced.

Provided that the temperature at the reactor pressure is at or below the boiling point of the hydrocarbon to be hydrogenated, the existing gas phase necessarily contains some other material in addition to said hydrocarbons, in this case hydrogen. This implies that where hydrogen is consumed inside the reactor it flows towards such region as long as there is a continuous gas phase present. Moreover, since the liquid phase (including the dissolved hydrogen) is in vapour-liquid equilibrium with the gas phase, the increase of the temperature is efficiently limited by the evaporation of the liquid. Thus the system remains in the desired temperature region with very little external control and any overheating of the catalyst is avoided.

A reactor operating in solely liquid or gas phase has not similar, inherent self-controlling properties. Because of the excellent mass transfer rate in the process according to the invention the reactor can be operated with small hydrogen excess. Because of this there is no need for hydrogen recirculation and thus recycle hydrogen compressor investment can be eliminated.

ADVANTAGES OF THE INVENTION

The process according to the invention has several further advantages. When a product obtained from dimerization, containing less than 15 wt-% of isobutylene trimers and tetramers and less than 5 wt-% oxygenates is used as a feed stock in the hydrogenation process according to the invention high olefin conversion is achieved at a relatively low operation pressure and temperature. The hydrogenation for olefin saturation and high product purity (low amount of oxygenates) described in the present invention can be applied for hydrogenation of a product from isobutylene dimerization with acidic catalysts. This can also be seen from the examples presented later. When a feed stock containing more than 90 wt-% of olefins is used the process is very effective.

According to the invention the hydrogenation of the above mentioned isooctene feed can be achieved with a small excess of hydrogen. The evaporation of isooctene/isooctane is so low at the selected operation temperature and pressure that the reactor can be operated in trickling or pulse flow state.

With the invention the hydrodynamic and reaction kinetic efficiency of the catalyst volume and reactor size can be adjusted separately at the different stages giving together the optimum for the hydrogenation. The trickle bed hydrogenation needs less catalyst volume than hydrogenation at a true gas or liquid phase reactor. The presented design is also more efficient than the traditional trickle bed reactor where the gas is as discontinuous phase and the liquid is as continuous phase.

The flow rates through different catalyst beds of the reactor may be significantly different. By using different particle sizes in different catalyst beds, it is possible to maintain the correct flow regime in all of them without other more complicated measures.

The amount of catalyst needed for the hydrogenation is smaller than that in conventional processes.

The excellent mass transfer within the reactor makes it possible to operate the hydrogenation with smallest possible hydrogen/olefin ratio. Actual hydrogen circulation compressor from the outlet is not usually needed.

The conversion of hydrogenation can be improved by introducing fresh hydrogen to the final hydrogenation stage and by conducting gas product from final hydrogenation stage to the first stage as can be seen from the optional embodiment presented in FIG. 2.

The overheating of the catalyst particles is avoided, which is a possible incident in a gas phase reactor.

The reaction temperature can be controlled by adjusting the pressure, whereby evaporative cooling takes place.

The proposed reactor concept brings economical benefit because of the compact design, especially in investment costs but also in operating costs.

When the reaction stages are in the same vessel, pressure difference is minimised because pressure difference is not needed for the pressure control.

The process according to the invention includes a reactor concept wherein all stages can be performed in the same housing because the catalyst bed dimensions are adjustable as a result of the varying of the particle size of the catalyst in each bed, which may comprise several layers. Also the hydraulics and mass transfer are adjustable.

By varying the feed site of hydrogen the partial pressure of hydrogen can be raised in the final reaction stage.

The invention is illustrated in more detail in the following examples as calculated, which are not meant to limit the scope of the invention, and variations and modifications are possible within the spirit the invention.

EXAMPLES

Examples 1 and 4 represent conventional processes, in examples 2 and 5 the diameter and the catalysts are the same in both stages and in examples 3 and 6 the particle size of the catalysts in the stages are different.

A fresh feed comprising 50000 kg/h of an olefin mixture, having C8—olefin content of 93.3 wt-% and C12—olefin content of 5.8 wt-% and fresh hydrogen feed of 975 kg/h are used in all examples. The same weight of the catalyst is used in the first reactor in examples 1-3 and in the second reactor in examples 1-3, and the same weight of the catalyst is used in the first reactor in examples 4-6 and in the second reactor in examples 4-6, respectively.

Example 1

Hydrogenation of the above mentioned feed mixture is performed. A catalyst comprising Pt/Alumina is used in all stages. The pressure is 3200 kPa (abs) after the second stage. The final olefin content is 1.7 wt-% The parameters of the process are provided in the following Table 1.

TABLE 1

| Parameter | First reaction stage | Second reaction stage |
|---|---|---|
| Particle size of the catalyst/mm | 4.5 | 4.5 |
| Reactor diameter/mm | 2900 | 2000 |
| Process conditions: Temperature (stage outlet)/° C. Pressure drop/kPa | 196 30 | 229 20 |
| Flow regime | Trickling/pulsing interphase | Trickling/pulsing interphase |

Example 2

Hydrogenation of the above mentioned feed mixture is performed. A catalyst comprising Pt/Alumina is used in all stages. The pressure is 3200 kPa (abs) after the second stage. The final olefin content is 2.5 wt-% The parameters of the process are provided in the following Table 2.

TABLE 2

| Parameter | First reaction stage | Second reaction stage |
|---|---|---|
| Particle size of the catalyst/mm | 4.5 | 4.5 |
| Reactor diameter/mm | 2900 | 2900 |
| Process conditions: Temperature (stage outlet)/° C. Pressure drop/kPa | 196 30 | 228 2 |
| Flow regime | Trickling/pulsing interphase | Channeling problems |

Example 3

Hydrogenation of the above mentioned feed mixture is performed. A catalyst comprising Pt/Alumina is used in all stages. The pressure is 3200 kPa (abs) after the second stage. The final olefin content is 1.9 wt-% The parameters of the process are provided in the following Table 3.

TABLE 3

| Parameter | First reaction stage | Second reaction stage |
| --- | --- | --- |
| Particle size of the catalyst/mm | 4.5 | 2 |
| Reactor diameter/mm | 2900 | 2900 |
| Process conditions: Temperature (stage outlet)/ ° C. Pressure drop/kPa | 196 30 | 229 15 |
| Flow regime | Trickling/pulsing interphase | Trickling/pulsing interphase |

Example 4

Hydrogenation of the above mentioned feed mixture is performed. A catalyst comprising Ni/Alumina is used all stages. The pressure is 3200 kPa (abs) after the second stage. The final olefin content is 1.7 wt-%. The parameters of the process are provided in the following Table 4.

TABLE 4

| Parameter | First reaction stage | Second reaction stage |
| --- | --- | --- |
| Particle size of the catalyst/mm | 3.2 | 3.2 |
| Reactor diameter/mm | 3300 | 2100 |
| Process conditions: Temperature (stage outlet)/ ° C. Pressure drop/kPa | 194 30 | 201 20 |
| Flow regime | Trickling/pulsing interphase | Trickling/pulsing interphase |

Example 5

Hydrogenation of the above mentioned feed mixture is performed. A catalyst comprising Ni/Alumina is used in all stages. The pressure is 3200 kPa (abs) after the second stage. The final olefin content is 2.3 wt-% The parameters of the process are provided in the following Table 5.

TABLE 5

| Parameter | First reaction stage | Second reaction stage |
| --- | --- | --- |
| Particle size of the catalyst/mm | 3.2 | 3.2 |
| Reactor diameter/mm | 3300 | 3300 |
| Process conditions: Temperature (stage outlet)/ ° C. Pressure drop/kPa | 194 30 | 199 5 |
| Flow regime | Trickling/pulsing interphase | Channeling problems |

Example 6

Hydrogenation of the above mentioned feed mixture is performed. A catalyst comprising Ni/Alumina is used in all stages. The pressure is 3200 kPa (abs) after the second stage. The final olefin content is 1.7 wt-%. The parameters of the process are provided in the following Table 6.

TABLE 6

| Parameter | First reaction stage | Second reaction stage |
| --- | --- | --- |
| Particle size of the catalyst/mm | 3.2 | 1.2 |
| Reactor diameter/mm | 3300 | 3300 |
| Process conditions: Temperature (stage outlet)/ ° C. Pressure drop/kPa | 194 30 | 201 30 |
| Flow regime | Trickling/pulsing interphase | Trickling/pulsing interphase |

The invention claimed is:

1. A Process for the hydrogenation of olefins which comprises hydrogenating a feed stock comprising more than 90 wt-% of olefins in one or more hydrogenation reactors comprising at least two reaction stages, wherein
   (a) the feed stock is hydrogenated in a first reaction stage having a cooling circuit and comprising at least a first catalyst bed, wherein fresh hydrogen is introduced to said first reaction stage;
   (b) the effluent from said first reaction stage being hydrogenated in a final reaction stage comprising at least one catalyst bed and optionally having a cooling circuit; and
   (c) the process being generated in a trickling or pulse flow mode in a three phase reactor with a fixed catalyst bed, wherein
      (i) at least one catalyst being utilized in each stage;
      (ii) the catalyst being utilized in said stages being of the same or different from that being used in other stages; and
      (iii) the catalyst being of a different particle size and/or different shape in at least two of said stages.

2. The process according to claim 1, wherein at least one catalyst bed of the first reaction stage is in a separate vessel before the hydrogenation reactor.

3. The process according to claim 1, wherein hydrogen is fed to the final reaction stage.

4. The process according to claim 1, wherein the feed stock comprises from 0 to 20 wt-% of C4 to C7 olefins, from 80 to 99 wt-% of C8 olefins and from 0 to 10 wt-% of heavier than C8 olefins.

5. The process according to claim 1, wherein the feed stock contains more than 50 wt % of di-isobutylene and/or tri-isobutylene, and optionally iso-butylene and n-butylene and codimers of iso-butylene and n-butylene.

6. The process according to claim 5, wherein the first reaction stage hydrogenation of the iso-butylene dimers in a reactor equipped with a cooling circuit is performed, and in the second stage hydrogenation of iso-butylene trimers is performed with an optional cooling circuit, each reaction stage consisting of one or multiple catalyst beds and the amount of layers per bed section being from one to three.

7. The process according to claim 1, said reactor being operated with not more than 40 mole % hydrogen excess and no circulating gas compressor is needed.

8. The process according to claim 1, wherein the diameter of the reactor vessel(s) before the final reactor is the same or not more than 50% larger than the one of the final reactor vessel.

9. The process according to claim 1, wherein the catalyst beds are in the same reactor vessel.

10. The process according to claim 1, wherein the catalyst beds are in different reactor vessels.

11. The process according to claim 1, wherein cooling of the reactor is accomplished with a cooling system located between the multiple catalyst beds.

12. The process according to claim 1, wherein different catalysts are used in the different catalyst beds.

13. The process according to claim 1, wherein the first catalyst bed of the reactor is protected by alkaline adsorption or absorption material.

14. The process according to claim 7, wherein the hydrogen excess is less than 20%.

15. The process according to claim 1, wherein more than 50 v/v % of the fresh hydrogen is introduced to the first reaction stage of the hydrogenation reactor.

16. The process according to claim 3, wherein more than 50 v/v % of the hydrogen is introduced to the final reaction stage of the hydrogenation reactor.

17. The process according to claim 1, wherein isooctane is hydrogenated.

18. The process according to claim 1, wherein said first and second reaction stages are conducted in the same hydrogenation reactor vessel.

19. The process according to claim 1, wherein the diameter of the reactor vessel(s) before the final reactor is the same or not more than 20% larger than the one of the final reactor vessel.

* * * * *